United States Patent [19]

Slatopolsky

[11] Patent Number: 4,948,789

[45] Date of Patent: Aug. 14, 1990

[54] SUPPRESSION OF PARATHYROID HORMONE SYNTHESIS AND SECRETION

[75] Inventor: Eduardo Slatopolsky, St. Louis, Mo.

[73] Assignee: Chugai Seiyaku Kabushiki Kaisha, Tokyo, Japan

[21] Appl. No.: 329,606

[22] Filed: Mar. 28, 1989

[51] Int. Cl.$^5$ .............................................. A61K 31/59
[52] U.S. Cl. .................................................... 514/167
[58] Field of Search ........................................ 514/167

[56] References Cited

FOREIGN PATENT DOCUMENTS 0184112 11/1985 European Pat. Off. .

OTHER PUBLICATIONS

Rollinson et al., "Mineral Nutrients", in *Kirk-Othmer Encyclopedia of Chemical Technology*, 3rd Edition, John Wiley & Sons, New York, vol. 15, p. 585, (1981).
Reiss et al., "Experience with a Radioimmunoassay of Parathyroid Hormone in Human Sera", *Trans. Assoc. Am. Physicians*, 81:104–115, (1968).
Arnaud, Claude D., "Hyperparathyroidism and Renal Failure", *Kidney International*, 4:89–95, (1973).
Slatopolsky et al., "Marked Suppression of Secondary Hyperparathyroidism by Intravenous Administration of 1,25-Dihydroxycholecalciferol in Uremic Patients", *J. Clin. Invest.*, 74:2136–2143, (1984).
Brown et al., "Abnormal Regulation of Parathyroid Hormone Release by Calcium in Secondary Hyperparathyroidism due to Chronic Renal Failure", *J. Clin. Endocrinol. Metab.*, 54:172–179, (1982).
Chertow, et al., "Decrease in Serum Immunoreactive Parathyroid Hormone in Rats and in Parathyroid Hormone Secretion", *J. Clin. Invest.*, 72:668–678, (1975).
Cantley et al., "1,25-Dihydroxyvitamin D$_3$ Suppresses Parathyroid Hormone Secretion from Bovine Parathyroid Cells in Tissue Culture", *Endocrinology*, 117:2114–2119, (1985).
Chan et al., "The Effect of 1,2 Dihydroxycholecalciferol on Parathyroid Hormone Secretion by Monolayer Cultures of Bovine Parathyroid Cells", *Calcif. Tissue Int.*, 38:27–32, (1986).
Silver et al., "Regulation by Vitamin D Metabolites of Messenger Ribonucleic Acid for Preproparathyroid Hormone in Isolated Bovine Parathyroid Cells", *Proc. Natl. Acad. Sci. U.S.A.*, 82:4270–4273, (1985).
Russell et al., "Suppression by 1,25(OH)$_2$D$_3$ of Transcription of the Pre-Proparathyroid Hormone Gene", *Endocrinology*, 119:2864–2866, (1986).
Silver et al., "Regulation by Vitamin D Metabolites of Parathyroid Hormone Gene Transcription in vivo in the Rat", *J. Clin. Invest.*, 78:1296–1301, (1986).
Ostrem et al., "24- and 26-homo-1,25-dihydrox- (List continued on next page.)

*Primary Examiner*—Joseph A. Lipovsky
*Attorney, Agent, or Firm*—Browdy and Neimark

[57] ABSTRACT

Vitamin D$_3$ derivatives of formula (I):

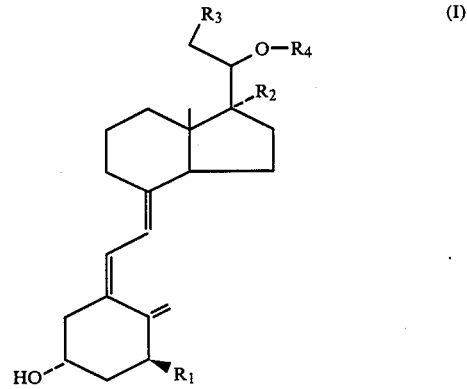

wherein R$_1$, R$_2$ and R$_3$, which may be the same or different, each represent a hydrogen atom or a hydroxyl group; R$_4$ is hydrogen or a C$_{4-6}$ alkyl group that is optionally substituted by a hydroxyl group; preferably 22-oxa-1,25-(OJ)$_2$D$_3$, or OCT, are administered to treat hyperparathyroidism, particularly secondary hyperparathyroidism, without inducing hypercalcemia. The derivatives may be administered orally or parenterally. They are preferably administered intravenously in the course of renal dialysis.

11 Claims, 5 Drawing Sheets

OTHER PUBLICATIONS yvitamin $D_3$: Preferential Activity in Inducing Differentiation of Human Leukemia Cells HL-60 in vitro", *Proc. Natl. Acad. Sci. U.S.A.*, 84:2610-2614, (1987).

Binderup et al., "Effects of Novel Vitamin D Analogue MC 903 on Cell Proliferation and Differentiation in vitro and on Calcium Metabolism in vivo", *Biochemical Pharmacology*, 37:889-895, (1988).

Abe et al., "Synthetic Analogues of Vitamin $D_3$ with an Oxygen Atom in the Side Chain Skeleton", *FEBS Lett.*, 226:58-62, (1987).

Murayama et al., "Synthetic Studies of Vitamin $D_3$ Analogues, VIII. Synthesis of 22-Oxavitamin $D_3$ Analogues", *Chem. Pharm. Bull.*, 34:4410-4413, (1986).

Hughes, et al., "Regulation of Serum $1\alpha,25$-Dihydroxyvitamin $D_3$ by Calcium and Phosphate in the Rat", *Science*, 190:578-580, (1975).

Garabedian et al., "Control of 25-Hydroxycholecalciferol Metabolism by Parathyroid Glands", *Proc. Nat. Acad. Sci. U.S.A.*, 69:1673-1676, (1972).

Salusky et al., "High-Dose Calcitriol for Control of Renal Osteodystrophy in Children on CAPD", *Kidney Int.*, 2:89-95, (1987).

Prior et al., "Experience with 1,25-Dihydroxycholecalciferol Therapy in Undergoing Hemodialysis Patients with Progressive Vitamin $D_2$-Treated Osteodystrophy", *The Amer. Jour. of Med.*, 67:583-589, (1979).

Berl et al., "1,25 Dihydroxycholecalciferol Effects in Chronic Dialysis-a Double-Blind Controlled Study", *Annals of Internal Medicine*, 88:774-780, (1978).

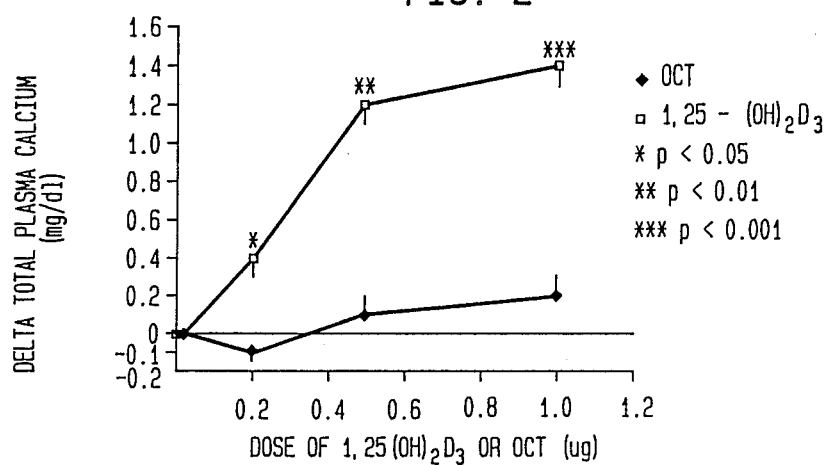
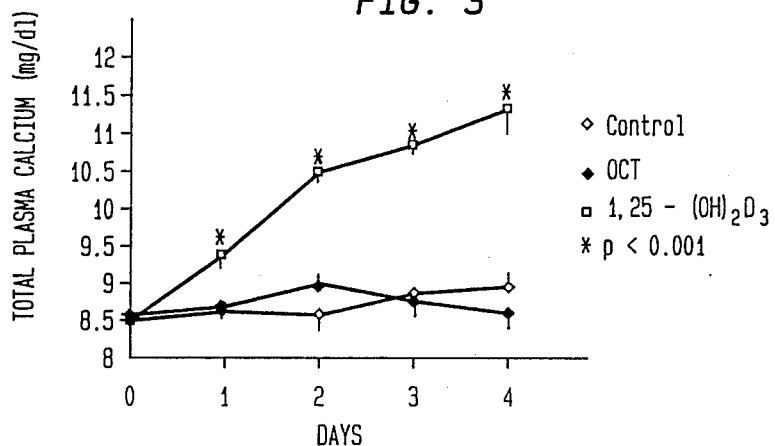

SUPPRESSION OF PARATHYROID HORMONE SYNTHESIS AND SECRETION

FIELD OF THE INVENTION

The present invention relates to a method and pharmaceutical compositions for treating hyperparathyroidism, and particularly secondary hyperparathyroidism, without inducing hypercalcemia.

BACKGROUND OF THE INVENTION

The active metabolite of vitamin D3 (cholecalciferol) is 1,25-dihydroxycholecalciferol (1,25-(OH)$_2$D$_3$). Parathyroid hormone (PTH) is produced by the parathyroid glands. The release of PTH is activated by a decrease in blood Ca$^{2+}$ level below normal. The production of 1,25-(OH)$_2$D$_3$ in the kidney requires the presence of 1-hydroxylase whose formation is induced by PTH. Since PTH acts upon the kidney to increase the production of 1,25-(OH)$_2$D$_3$, it appears that a negative feedback system could operate to regulate PTH secretion. The absorption of calcium from the intestine into the blood requires, for transport, a calcium-binding protein (CaBP). Synthesis of CaBP is activated by 1,25-(OH)$_2$D$_3$. Both PTH and 1,25-(OH)$_2$D$_3$ are active in the increase of blood Ca$^{2+}$ concentration by increasing resorption of calcium from bone. The interrelationship of blood Ca$^{2+}$ concentration, PTH levels and 1,25(OH)$_2$D$_3$ levels is shown in FIG. 1 which is published in Rollinson et al "Mineral Nutrients", in *Kirk-Othmer Encyclopedia of Chemical Technology*, 3rd edition, John Wiley & Sons, New York, vol. 15, page 585, 1981. In this figure, CC is cholecalciferol (vitamin D$_3$), HCC is hydroxycholecalciferol, DHCC is 1,25-(OH)$_2$D$_3$ and NADPH is protonated nicotinamide-adenine dinucleotide phosphate.

Secondary hyperparathyroidism is a universal complication of chronic renal insufficiency (cf. Reiss et al., *Trans. Assoc. Am. Physicians*, 81:104–115, 1968; Arnaud, *Kidney Int.* 4:89–95, 1973). In severe renal insufficiency, the lack of 1,25-(OH) becomes a factor in maintaining the hypersecretion of PTH.

The suppressive effect of 1,25-(OH)$_2$D$_3$ on pTH secretion has led to its use for treatment of secondary hyperparathyroidism. Administration of 1,25-(OH)$_2$D$_3$ was found to lower PTH levels in hemodialysis patients more effectively than calcium, even when both substances raised ionized calcium to the same degree (Slatopolsky et al., *J. Clin. Invest.*, 74:2136–2143, 1984). Parathyroid cells from patients with secondary hyperparathyroidism are less sensitive to the suppressive effects of calcium (Brown et al., *J. Clin. Endocrinol. Metab.*, 54:172–179, 1982). Furthermore, it appears that intravenous 1,25-(OH)$_2$D$_3$ treatment of renal failure patients shifts the set point for calcium toward more normal values (Delmez et al., *J. Clin. Invest.*, 1989, in press).

Although 1,25-(OH)$_2$D$_3$ is now commonly used to treat hyperparathyroidism associated with renal failure, and particularly patients undergoing renal dialysis, its prolonged use is precluded in some cases by hypercalcemia. This is compounded by the fact that calcium carbonate is currently the preferred compound for binding of intestinal phosphorus, which is mandatory before vitamin D is administered to uremic patients. Calcium carbonate is the phosphate-binder of choice since phosphate binders containing aluminum frequently induce aluminum accumulation, with its well known deleterious effects. Unfortunately, the simultaneous administration of large doses of calcium carbonate and 1,25-(OH)$_2$D$_3$ frequently induces severe hypercalcemia, thus precluding the administration of therapeutic doses of 1,25-(OH)$_2$D$_3$.

More recently, the suppressive action of 1,25-(OH)$_2$D$_3$ on parathyroid hormone synthesis and secretion has been better defined. It has been suggested that 1,25-(OH)$_2$D$_3$ can suppress PTH directly, independent of calcium (Chertow et al, *J. Clin. Invest.*, 72:668–678, 1975). Primary cultures of bovine parathyroid cells have been used to demonstrate that 1,25-(OH)$_2$D$_3$ inhibits release of PTH (Cantley et al., *Endocrinology*, 117:2114–2119, 1985; Chan et al, *Calcif. Tissue Int.*, 38:27–32, 1986), decreases the levels of pre-proPTH mRNA (Silver et al, *Proc. Natl. Acad. Sci. USA*, 82:4270–4273, 1985), and blocks transcription of the PTH gene (Russell et al, *Endocrinology*, 119:2864–2866, 1986). This inhibition of transcription in vivo may not be secondary to an increase in serum calcium (Silver et al, *J. Clin. Invest.*, 78:1296–1301, 1986). The close correlations between PTH release and the decrease in pre-proPTH mRNA, and the lack of an acute effect of 1,25-(OH)$_2$D$_3$ indicates that 1,25-(OH)$_2$D$_3$ acts at the transcriptional level. Furthermore, since physiological concentrations ($10^{-11}$M) of 1,25-(OH)$_2$D$_3$ in the culture medium suppressed release and synthesis of PTH, it seems likely that conditions in which 1,25-(OH)$_2$D$_3$ levels are abnormally low, e.g., renal failure, would lead to increases in serum PTH.

A number of analogs of 1,25-(OH)$_2$D$_3$ have been synthesized that have little calcemic activity but retain the ability to differentiate myeloid leukemia cells. 24-Homo-1,25-(OH)$_2$D$_3$ can differentiate HL-60 cells without increasing serum calcium when administered to vitamin D-deficient rats (Ostrem et al, *Proc. Natl. Acad. Sci. USA*, 84:2610–2614, 1987). Similar differential activity occurs with MC903, a 1,25-(OH)$_2$D$_3$ analog with a cyclopropyl group at the end of the side chain (Binderup et al, *Bioch Pharmacology*, 37:889–895, 1988). Furthermore, 22-oxa-1,25-(OH)$_2$D$_3$, also known as 22-oxa-calcitrol or OCT, has been shown to differentiate HL-60 with very low bone calcium mobilizing activity in vitro (Abe et al, *FEBS Lett.*, 226:58–62, 1987). This compound also has no calcemic activity in vivo (Murayama et al, *Chem. Pharm. Bull.*, 34: 4410–4413, 1987). Analogs including OCT are described in EP 0 184 112. There have been no reports to date as to the ability of any non-calcemic analog of 1,25-(OH)$_2$D$_3$ to emulate the activity of 1,25-(OH)$_2$D$_3$ in regulation of hyperparathyroidism.

Because of the known interrelationship among serum Ca$^{2+}$, PTH and 1,25-(OH)$_2$D$_3$ levels, because of the unknown effects on PTH production caused by varying the structure of the 1,25-(OH)$_2$D$_3$ molecule, and because of the lack of any evidence correlating myeloid leukemia cell differentiation ability of 1,25-(OH)$_2$D$_3$ analogs with their effect on PTH transcription, there is no predictability as to the ability of any given analog of 1,25-(OH)$_2$D$_3$ to affect hypersecretion of PTH. Furthermore, since the action of 1,25-(OH)$_2$D$_3$ is mediated by a cellular receptor that is believed to be identical in all tissues, and since OCT binds to the chick intestinal receptor fourteen times less avidly than 1,25-(OH)$_2$D$_3$ (Murayama et al, 1987, supra) and is less active in raising serum calcium, the equivalent activity of OCT and 1,25-(OH)$_2$D$_3$ in parathyroid glands is surprising and would not have been predicted.

SUMMARY OF THE INVENTION

It is an object of the present invention to overcome the above-noted deficiencies in the prior art.

It is another object of the present invention to provide a method for suppressing the secretion and synthesis of PTH.

It is yet another object of the present invention to provide a method for treating secondary hyperparathyroidism without inducing hypercalcemia.

According to the present invention, PTH synthesis and secretion may be suppressed by the administration of a vitamin D derivative of formula (I):

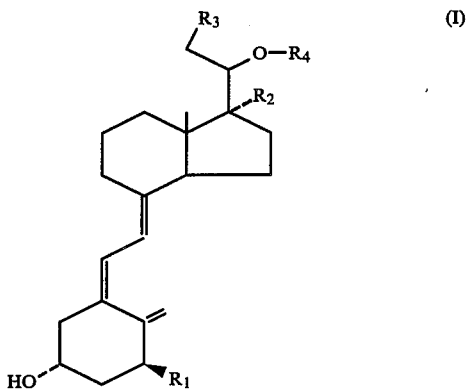

wherein R$_1$, R$_2$ and R$_3$, which may be the same or different, each represent a hydrogen atom or a hydroxyl group; R$_4$ is hydrogen or a C$_{4-6}$ alkyl group that is optionally substituted by a hydroxyl group. Thus, such derivatives would be expected to be useful in the treatment of secondary hyperparathyroidism. The preferred such derivative is 22-oxa-1,25-(OH)$_2$D$_3$, or OCT. OCT has been found to be slightly more active in suppressing PTH release than the parent compound which is currently used for this treatment, 1,25-(OH)$_2$D$_3$. It is expected that all of the other closely related derivatives of formula (I) also have a significant effect in suppressing PTH release. However, all of these derivatives, unlike the parent compound, have very little calcium mobilizing activity, and thus do not lead to hypercalcemia.

Thus, all of the derivatives of formula (I), and particularly OCT, are valuable agents for treating secondary hyperparathyroidism

BRIEF DESCRIPTION OF THE DRAWINGS

FIG. 2 shows calcemic response to various doses of OCT and 1,25-(OH)$_2$D$_3$.

FIG. 3 shows calcemic response to chronic administration of OCT and 1,25-(OH)$_2$D$_3$.

DETAILED DESCRIPTION OF THE INVENTION

Figure 1:
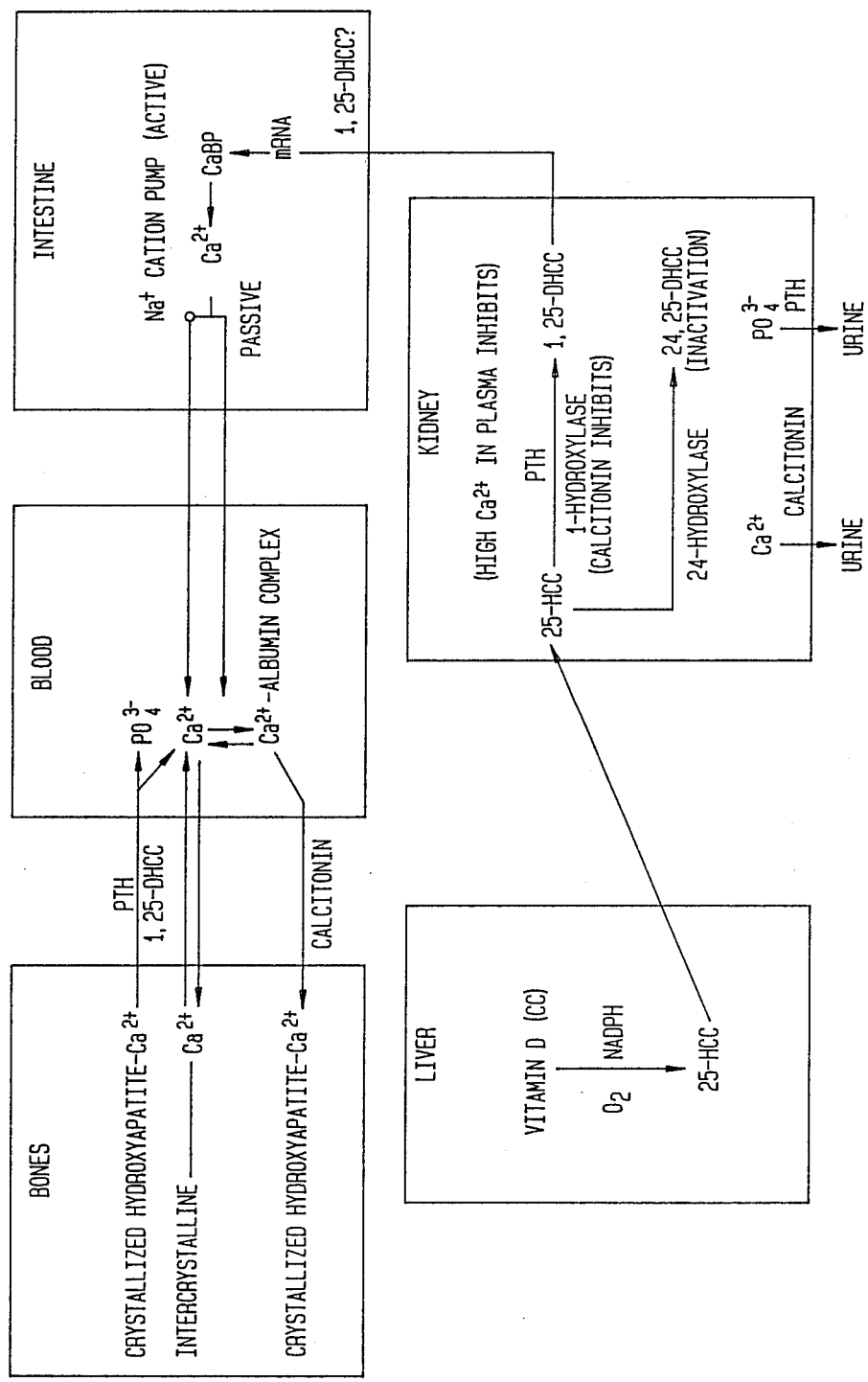
FIG. 1 shows the interrelationship of serum Ca$^{2+}$, PTH and 1,25-(OH)$_2$D$_3$ production and regulation in vivo.

The present invention relates to the discovery that OCT, notwithstanding its lack of calcemic activity and notwithstanding its substantial inability to bind to the chick intestinal receptor as compared to 1,25-(OH)$_2$D$_3$, is effective in the suppression of PTH synthesis and secretion and thus will be effective in the treatment of hyperparathyroidism, and particularly secondary hyperparathyroidism associated with renal failure. The present invention further relates to the realization that all of the closely related derivatives of formula (I) will have substantially the same properties in this regard as has OCT.

Calcemic Response:

The lack of calcemic activity of OCT was confirmed by acute and chronic administration of OCT to normal rats. A single intraperitoneal injection of propylene glycol vehicle, OCT, or 1,25-(OH)$_2$D$_3$ in the quantity of 1.0 µg/rat increased calcium by 0.32, 0.30, and 1.40 mg/dl, respectively. When the rats were given daily injections of the propylene glycol vehicle or 0.5 µg of either 1,25-(OH)$_2$D$_3$ or OCT for four days, the calcium did not change in the rats receiving vehicle or OCT, but increased from 8.4 to 11.4 mg/dl in the rats treated with 1,25-(OH)$_2$D$_3$.

In primary cultures of bovine parathyroid cells, 10 nM OCT was as active as 10 nM 1,25-(OH)$_2$D$_3$, suppressing PTH release by 33%. This suppression is due, at least in part, to blocking transcription of the PTH gene.

The acute calcemic response to OCT and 1,25-(OH)$_2$D$_3$ was determined in normal male Sprague-Dawley rats (250–275 g) fed a standard chow diet containing 1.0% calcium and 0.4% phosphorus. At 24 hours following a single intraperitoneal injection of 250 µl propylene glycol vehicle, or 0.2, 0.5, or 1.0 µg of 1,25-(OH)$_2$D$_3$ or OCT, blood was taken to measure the calcium levels. The increment in plasma calcium, calculated by subtracting the pre-dose calcium value from the 24 hour post-dose value for each rat, was determined for each dose of 1,25-(OH)$_2$D$_3$ or OCT.

The calcemic response to these doses is shown in FIG. 2. The delta serum calcium values Were calculated as described above. All values are expressed as mean+S.E.M., n=4.

For the chronic studies, normal male rats (300 g, on the standard chow diet) received daily intraperitoneal injections of 250 µl propylene glycol vehicle or 0.5 µg of either 1,25-(OH)$_2$D$_3$ or OCT. Following a five hour fast each morning, the rats were weighed, a blood sample was taken from the tail vein to measure calcium, and the next injection was given. These results are shown in FIG. 3, where all values are expressed as mean±S.E.M., n=6. A paired t test was used to determine statistical differences between control and treated samples.

PTH Secretion in Cultured Bovine Parathyroid Cells:

Primary cultures of bovine parathyroid cells were prepared as described by Brown et al in *Endocrinology*, 99:1582–1588, 1972, With modifications as described by Morrissey et al, *Endocrinology*, 103:2081–2090, 1978. After five days in culture, the cells were treated with various concentrations of 1,25-(OH)$_2$D$_3$ or OCT. Both compounds were aliquotted as ethanol solutions (ethanol alone for controls), dried under nitrogen, and vortexed into the culture media. The cells were incubated with media containing 1,25-(OH)$_2$D$_3$ or OCT for 48 hours with a media change after 24 hours.

Figure 4:
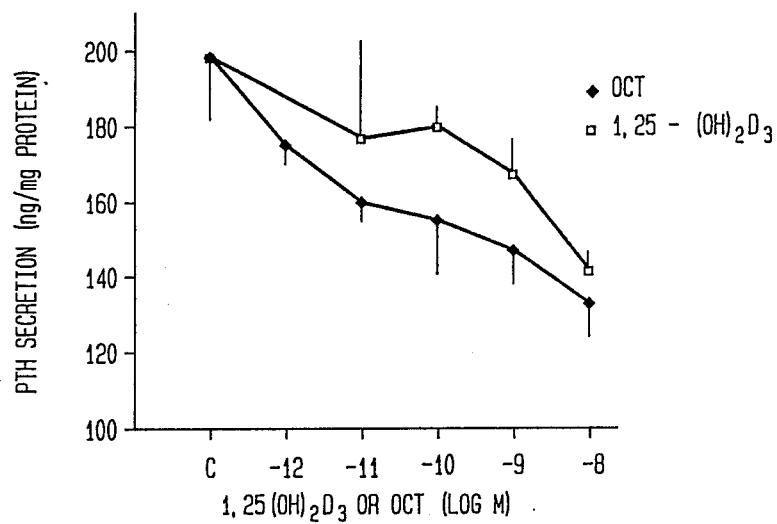
FIG. 4 shows the effects of OCT and 1,25-(OH)$_2$D$_3$ on PTH secretion from primary cultures of bovine parathyroid cells.

To determine the rate of PTH secretion, the cells were washed twice, and then incubated for three hours in fresh media at 37° C. The media was centrifuged and assayed for PTH by radio-immunoassay using an antibody (CH9) that recognizes the intact, middle, and C-terminal regions of bovine PTH (cf. Hruska et al, *J. Clin. Invest.*, 56:39–48, 1975). Protein in each sample was determined by sonicating the cells into 1 M sodium hydroxide and assaying an aliquot by the method of Bradford, *Anal. Biochem.*, 72:248–254, 1976. These results are shown in FIG. 4. The media samples were centrifuged and assayed for PTH by radioimmunoassay. All PTH values were corrected for cell protein and expressed as mean±S.E.M., n=4.

Pre-proPTH mRNA Levels in Rat Parathyroid Glands:

Normal rats fed standard chow diets were given a single intraperitoneal injection of 250 μl propylene glycol vehicle or 100 pmol of either 1,25-(OH)$_2$D$_3$ or OCT. After 40 hours, the rats were anesthetized with chloral hydrate, blood was taken from the aorta, and the parathyroid glands were removed and placed immediately in liquid nitrogen.

An 800 bp MspI fragment of plasmid PTHm122 was labelled to a specific activity of about 10$^9$ cmp/μg using a random primed kit. A synthetic oligonucleotide probe to rat cytoplasmic β-actin was labelled to a specific activity of about 10$^7$ cmp/μg by a 5' end-labelling kit using T4 kinase.

To determine pre-proPTH mRNA levels, extracts of cytoplasmic RNA were prepared from a pool of 16 rat parathyroid glands. The previously frozen glands were homogenized in 45 μl of 10 mM Tris-HCl, 1 mM EDTA, pH 8, and 5 μl of 5% NP40 was added. After five minutes on ice, the homogenate was centrifuged in a microfuge at 4° C. for five minutes. The supernatant was removed and mixed with 30 μl of 20X SCC (1X SCC is 0.15 M sodium chloride, 0.01 M sodium citrate, pH 7) and 20 μl of 37% formaldehyde, and incubated at 60° C. for fifteen minutes. Dilutions of the extracts were applied to nitrocellulose in a slot blot apparatus, and the filter was baked at 80° C. for two hours under vacuum. The filters were prehybridized in 5X SSC, 5X Denhardt's, 100 μg/ml salmon tested DNA in 50% formamide at 42° C. for three hours. The filters were then placed in the appropriate hybridization solution of 5X SSC, IX Denhardt's, 100 μg/ml salmon testes DNA, 10% dextran sulfate in 50% formamide containing 10$^6$ cpm/ml of either the PTHm122 probe or the β-actin oligonucleotide probe. The hybridization was carried out overnight at the less stringent room temperature, since there are differences in the DNA sequence between the human PTH cDNA probe and the rat pre-proPTH RNA. The filters were washed the next day at room temperature once in 4X SSC, 0.1% sodium dodecyl sulfate, and three times in IX SSC, 0.1% sodium dodecyl sulfate before drying and subsequent autoradiography. Again, this less stringent wash was used so as not to obliterate the species difference between the cDNA probe and the desired measurement of mRNA. As a control, cytoplasmic RNA extracts from 10 mg of rat liver, prepared as described above, were assayed in an identical manner.

Figure 5:
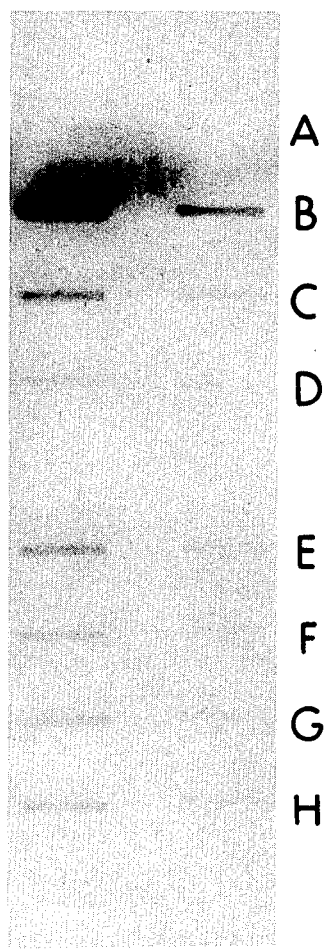
FIG. 5 shows slot-blot analysis of cytoplasmic RNA extracted from liver and from parathyroid glands.

FIG. 5 shows the slot-blot analysis of cytoplasmic RNA extracted from liver (A and E), and from parathyroid glands from control rats (B and F), 1,25-(OH)$_2$D$_3$-treated rats (C and G), and OCT-treated rats (D and H). Slots A-D were hybridized with PTHm122 cDNA, while slots E-H were hybridized with a rat k5 bk1-actin oligonucleotide cDNA. The left side represents twice as much RNA extract as the right side.

Figure 6:
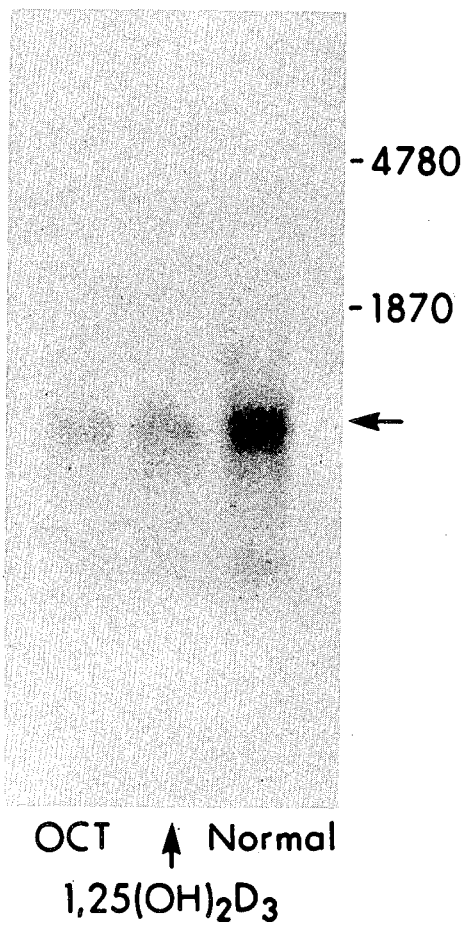
FIG. 6 shows Northern blot analysis of cytoplasmic RNA extracted from parathyroid glands.

To perform the Northern blot anaylsis, a portion of the cytoplasmic RNA pool extracted from the rat parathyroid glands was treated with phenol, ethanol precipitated with carrier tRNA, and subjected to electrophoresis on a 1.2% agarose gel containing formaldehyde. The RNA was transferred to nitrocellulose by capillary action; the nitrocellulose was baked, prehybridized, and hybridized with PTHm122 cDNA as described above. The migration of ribosomal RNA was determined by ethidium bromide staining of an adjacent lane in the agarose gel containing a liver RNA extract. FIG. 6 shows this Northern blot analysis.

From the above, it can be seen that OCT is active in vivo and, like 1,25-(OH)$_2$D$_3$, decreases pre-proPTH mRNA levels. Thus, the lack of calcemic activity is not the results of rapid metabolism or clearance of OCT.

While the specific examples described above all specifically relate to the use of the preferred embodiment of the present invention, i.e., OCT, the present invention is intended to comprehend not only the use of such preferred compound but also the use of all of the other vitamin D$_3$ derivatives of formula (I), all of which are closely structurally related to OCT inasmuch as all are 22-oxa-vitamin D$_3$ derivatives. All of the compounds of formula (I) are described in detail, and their methods of synthesis are disclosed, in EP 0 184 112 and its corresponding U.S Pat. No. 4,891,364 issued Jan. 2, 1990, the entire contents of both of which are hereby incorporated herein by reference. Those of ordinary skill in this art will recognize and expect that all of these closely related 22-oxa-vitamin D$_3$ derivatives will have substantially the same superior properties as OCT, described above, and thus can also be used in the methods and compositions of the present invention with substantially the same advantageous results.

In treating patients with secondary hyperparathyroidism according to the present invention, the compound of formula (I), preferably OCT, may be given orally or parenterally. However, intravenous administration is preferable in order to obtain a greater delivery of the compound to peripheral target tissues rather than to the intestine. Furthermore, it is convenient to administer the compound intravenously in the course of renal dialysis, as the intravenous needles are already in place.

The intravenous dose of the compounds of formula (I) can range from about 1 μg to 10 μg during each dialysis treatment. In general, dialysis treatments are performed three times per week. If administered daily the oral or other parenteral dose of the compound can range from 0.5 μg to 5 μg daily. If, during the course of treatment, there appears an abatement of the symptoms of the condition being treated, the daily dosage can be diminished to as much as one tenth the initially prescribed amount. In such a case the daily dose may be as small as 0.05 μg per day. Effective doses for each patient can readily be determined empirically for each of the compounds of formula (I) by observing the effect on PTH secretion caused by the administration of the compound and maintenance of a normal serum calcium level. The determination of specific effective dosages for each such compound is therefore within the skill of the art.

Pharmaceutical compositions according to the present invention for treating hyperparathyroidism, and particularly secondary hyperparathyroidism, include compositions wherein the compound of formula (I) is contained in an amount sufficient to achieve its intended purpose. Determination of the effective amount is well within the skill in the art.

In addition to the compounds of formula (I), these pharmaceutical compositions may contain suitable pharmaceutically acceptable carriers comprising excipients and auxiliaries which facilitate processing of the active compounds into preparations which can be used pharmaceutically. Preferably, the preparations, particularly those which can be administered orally, such as tablets, dragees, and capsules, and also preparations which can be administered rectally, such as suppositories, as well as suitable solutions for administration by injection or orally, contain from about 0.1 to 99 percent, preferably from about 25–85 percent, of active compound, together with the excipient.

The pharmaceutical preparations of the present invention are manufactured in a manner which is itself known, for example, by means of conventional mixing, granulating, dragee-making, or dissolving processes. Thus, pharmaceutical preparations for oral use can be obtained by combining the active compounds with solid excipients, optionally grinding a resulting mixture, and processing the mixture of granules, after adding suitable auxiliaries, if desired or necessary, to obtain tablets or dragee cores.

Suitable excipients are, in particular, fillers such as sugars such as lactose, sucrose, mannitol, or sorbitol, cellulose preparations, and/or calcium phosphates such as tricalcium phosphate or calcium hydrogen phosphate. Binders for use in the compositions according to the present invention include starch paste using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added such as the above-mentioned starches as well as carboxymethyl starch, cross-linked polyvinylpyrrolidone, agar, or alginic acid or a salt thereof such as sodium alginate. Auxiliaries include flow-regulating agents and lubricants, such as silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated sugar solutions may be used, which may optionally contain gum arabic, talc, polyvinyl pyrrolidone, polyethylene glycol, and/or titanium dioxide, lacquer solutions, and suitable organic solvents or solvent mixtures. In order to produce coatings resistant to gastric juices, solutions of suitable cellulose preparations such as acetyl-cellulose phthalate or hydroxypropylmethylcellulose phthalate, are used. Dyestuffs or pigments may be added to the tablets or dragee coatings, for example, for identification or in order to characterize different combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be added.

Suitable formulations for parenteral administration include aqueous solutions of the active compounds in water-soluble form. In addition, suspensions of the active compounds as appropriate oily injection suspensions may be administered. Suitable lipophilic solvents or vehicles include fatty oils such as sesame oil, or synthetic fatty acid esters such as ethyl oleate or triglycerides. Aqueous injection suspensions may contain substances which increase the viscosity of the suspension such as sodium carboxymethyl cellulose, sorbitol, and/or dextran. Optionally, the suspension may also contain stabilizers.

It will be obvious to those skilled in the art that various changes may be made without departing from the scope of the invention, and that the invention is not to be considered limited to what is shown in the drawings and described in the specification.

WHAT IS CLAIMED IS:

1. A method for treating hyperparathyroidism comprising administering to a patient suffering from hyperparathyroidism an effective amount of a vitamin $D_3$ derivative of formula (I):

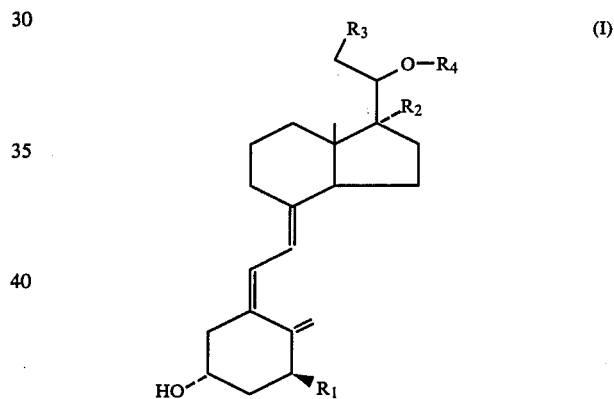

wherein $R_1$, $R_2$ and $R_3$, which may be the same or different, each represent a hydrogen atom or a hydroxyl group; $R_4$ is hydrogen or a $C_{4-6}$ alkyl group that is optionally substituted by a hydroxyl group.

2. The method of claim 1 wherein the derivative is administered intravenously.

3. The method of claim 1 wherein the derivative is administered orally.

4. The method of claim 1, wherein the patient further suffers from chronic renal insufficiency and the hyperparathyroidism is secondary hyperparathyroidism.

5. The method of claim 4, wherein the patient is undergoing renal dialysis and wherein the derivative is administered during each renal dialysis.

6. The method of claim 5 wherein the derivative is 22-oxa-1,25-$(OH)_2D_3$.

7. The method of claim 1 wherein the derivative is administered in an initial amount corresponding to about 0.5 μg to about 5 μg daily.

8. The method of claim 7 wherein the derivative is administered intravenously three times per week in an initial amount of about 1 μg to about 10 μg per dose.

9. The method of claim 1 wherein the derivative is 22-oxa-1,25-(OH)$_2$D$_3$.

10. The method of claim 9 wherein the 22-oxa-1,25(OH)$_2$D$_3$ is administered in an initial amount corresponding to about 0.5 μg to about 5 μg daily.

11. The method of claim 10 wherein the 22-oxa-1,25-(OH)$_2$D$_3$ is administered intravenously three times per week in an initial amount of about 1 μg to about 10 μg per dose.

* * * * *